United States Patent [19]

Hirs

[11] 4,190,533

[45] Feb. 26, 1980

[54] FILTER METHOD

[75] Inventor: Gene Hirs, Livonia, Mich.

[73] Assignee: AMSTED Industries Incorporated, Chicago, Ill.

[21] Appl. No.: 657,666

[22] Filed: Feb. 12, 1976

[51] Int. Cl.$^2$ .............................................. B01D 23/24
[52] U.S. Cl. ......................................... 210/80; 210/82
[58] Field of Search ..................... 210/79, 80, 82, 263, 210/274, 275, 290, 503, 510

[56] References Cited

U.S. PATENT DOCUMENTS

| 293,745 | 2/1884 | Hyatt ..................................... 210/290 |
| 3,343,680 | 9/1967 | Rice et al. ............................. 210/263 |
| 3,382,983 | 5/1968 | Stewart ............................. 210/290 X |
| 3,424,674 | 1/1969 | Webber ............................. 210/80 X |
| 3,471,025 | 10/1969 | Dobson ........................... 210/290 X |
| 3,497,068 | 2/1970 | Hirsch ............................. 210/290 X |
| 3,544,457 | 12/1970 | Tulley et al. ........................ 210/500 |
| 3,704,786 | 12/1972 | Lerner et al. ........................ 210/290 |
| 3,734,295 | 5/1973 | Smith et al. ...................... 210/290 X |
| 3,814,247 | 6/1974 | Hirs .......................................... 210/80 |
| 3,876,546 | 4/1975 | Hsiung et al. ....................... 210/275 |

*Primary Examiner*—Charles N. Hart
*Assistant Examiner*—Ivars Cintins
*Attorney, Agent, or Firm*—Edward J. Brosius; Fred P. Kostka

[57] ABSTRACT

A filtration method and apparatus for removing contaminants from liquids, including a deep bed filter comprised of either a single media layer or of two or more vertically superimposed, substantially distinct, contiguous layers of filter material. In the plural layer deep bed filters the lower layers typically consist of materials such as sand or anthracite, which are inherently comprised of nonuniform filter granules, even when graded or sieved to within a fairly restricted mesh size range. The upper layer in the plural layer filters is comprised of filter media granules having substantially identical configurations and sizes to achieve a high layer porosity for reducing the rate of back pressure buildup during the filtration cycle. Additionally, the media granules of the upper layer preferably have a specific gravity of between about 1.05 and 1.4, are preferentially hydrophilic, i.e., water-wetted, as opposed to preferentially oleophilic, and are preferentially cylindrical. One specific example of a filter material having all these characteristics includes hollow glass tubes sealed at both ends. Such materials may also be used advantageously as the sole material in a single layer deep bed filter.

The method includes backwashing the filter by flowing liquid upwardly through the filter media to expand the layer or layers substantially in situ. Afterwards, the layers are reformed. Due to the uniformity in size and shape of the filter material, the top layer is reformed with substantially the same porosity at its inlet surface as existed prior to the preceding filtration cycle.

1 Claim, No Drawings

FILTER METHOD

BACKGROUND OF THE INVENTION

This disclosure relates very generally to a deep bed filter having one or more media layers that are backwashed substantially in place by reverse liquid flow.

Deep bed filters have evolved through the years and have become more efficient and capable of handling variable filter operating conditions. For example, probably one of the most widely used filters through the years has been the mono-bed filter comprised of sand. Sand, however, has its drawbacks because it consists of a distribution of different grain sizes, even when sieved to within a fairly restricted mesh size range. This grain size distribution results in a classification or stratification of granules during backwash. More specifically, in the backwashing step the filter bed is expanded and the lighter smaller materials tend to rise to the top and the heavier larger materials tend to gravitate to the bottom. Therefore, materials are classified with the finest filter particles in the top of the filter and the coarsest filter particles in the bottom.

One of the most ideal ways for a deep bed filter to operate is to have the influent go through the coarsest layer first and then through progressively finer filter media layers. However, in the normal down-flow, mono-bed filter the least ideal condition exists as the flow is from the finest to the coarsest. This often creates a condition that the incoming contaminant cannot penetrate the inlet surface and a plugging, or surface loading, condition occurs. This creates a fast pressure rise and puts the filter out of condition in an abnormally short period of time, requiring premature backwashing.

The next step in the improvement of the mono-bed filter was the advent of the dual media filters. These filters typically consist primarily of a top layer of anthracite and a bottom layer of sand, the anthracite being lighter and larger than the sand, and the sand consisting generally of the same size particles as used in the mono-bed. The dual media filters of this type provide at least two advantages over the mono-media filter. First, the anthracite presents a more open and porous surface to the influent, thus allowing coarser particulates to penetrate the surface. Second, a mixing at the interface between the two medias results in a more porous strata at the top of the layer of sand, again allowing penetration into the sand bed. This arrangement, even though both media tend to classify, is far superior because of the larger, lighter anthracite on the surface and is now the most accepted dual media filter in the art. Even though there is far less surface plugging tendency in this arrangement than in the mono-bed, high concentration of dirt and lint like materials still surface load and plug this type of filter fairly easily.

The basic dual media filter has been modified in various respects, for example by adding a material with a greater specific gravity and finer grain size than the sand, as shown in U.S. Pat. No. 3,343,680. The finer, heavier material represents the bottom media, the second being sand and the top anthracite. The size of the top two materials is similar to that used in the standard dual-media concept. This concept allows somewhat finer filtration and minimizes breakthrough; however, it is still subject to the problem of surface load plugging, as discussed above.

Another concept is shown in Applicant's earlier U.S. Pat. No. 3,695,433, where a large organic polymeric material in the size range of 2.5 to 6.5 millimeters is disclosed for a mono-bed. This arrangement was successful in removing heavy loads and lint like materials, however, was somewhat lacking in a high enough percentage of removal of fine materials. Therefore, in some environments, this filter had to be followed up with an additional polishing filter such as a dual-media filter. Two distinct filters were required because the plastic beads had to be backwashed by recirculation through external means and therefore would not fit in with the normal flow backwash technique used in standard filters.

Further modification of this principle is shown in Applicant's U.S. Pat. No. 3,814,425 in which large organic polymeric materials were used on top of a layer of sand. This was effective in filtration and did not plug up from concentrated loads and lint like materials. However, backwashing was difficult because the sand had to be backwashed in situ and the organic particles had to be recirculated and backwashed outside of the filter. This created a problem of balancing a flow for the proper quantity of water to expand the sand and this quantity had to be removed at the same time by external scrubbers. The flow equilibrium, although not impossible, was difficult to achieve as changes of temperature had a pronounced effect on the overall results.

There have been other efforts to overcome heavy dirt loads and plugging materials coming to deep bed polishing filters. However, most of these techniques have depended upon gravity settling and various techniques of coagulation to reduce the dirt load. Most of the time this condition is impossible to control. Such is the case with a sanitary system where the equilibrium is upset when a storm or an abnormal condition occurs or when a toxic material is accidentally dumped into a sanitary system. When a condition of this nature occurs, the clarifiers, which are in a delicate equilibrium, are completely upset and the sludge blanket tends to overflow to the filters. The normal practice is to immediately divert this flow away from the filters and most of the time this high concentration of contaminants is dumped into the streams. The inadequacy of the current filters therefore is quite evident in occurrences of this nature.

SUMMARY OF THE INVENTION

The present invention overcomes these prior art problems and disadvantages in one preferred embodiment by a deep bed filter which is comprised of at least two vertically superimposed, contiguous, granular filter media layers intermixed at a contacting interface. The lower filter media layer typically consists essentially of nonuniform granules, such as sand or anthracite, which have a specific gravity greater than about 1.4. The upper filter media layer consists essentially of granules being highly uniform in both size and configuration. More preferably, the granules of the upper filter media will have one or more of the following characteristics: the granules (1) will be substantially symmetrical, (2) will have a specific gravity less than about 1.4, (3) will be coarser than the granules in the lower layer and (4) will be water-wetted. This particular set of characteristics provides a highly porous top filter media layer that reduces the rate of back pressure buildup during filtration flow and that can be backwashed substantially in place by expansion during reverse liquid flow.

In more preferred embodiments, the granules of the upper filter layer in the multiple layer filter are cylindrical and have a uniformity coefficient of substantially one, where the uniformity coefficient is defined as the ratio of the sieve opening, in millimeters, which will pass sixty percent of the granules to the sieve opening, in millimeters, which will pass just ten percent of the granules.

In another preferred embodiment of this invention, the deep bed filter is comprised of a single layer of media having the same characteristics as the media of the top layer in the multiple layer bed previously discussed.

Specific filter materials proposed by this invention include nitrile-rubber, polysulfide rubber, polyurethane and glass. Granules of these first three materials may be formed by conventional extrusion and chopping techniques. Glass, however, typically has a specific gravity of about 2.6. Therefore, to achieve the preferred specific gravity in the range of about 1.05 to about 1.4, the glass media granules may be formed as hollow glass cylinders having sealed ends. The most ideal cylindrical granule size will include a diameter and a length in the range of from about 3/16 to about ¼ inch. Alternatively, the granules may be spherical, in which case the most preferred size will include a diameter in the range of from about 3/16 to about ¼ inch.

The method of this invention includes flowing contaminated liquid through media layers in a deep bed filter, comprised of the materials previously described. After the filter has accumulated a substantial amount of contaminants within the interstices of the filter media, the contaminated liquid flow is terminated and the deep bed filter is rejuvenated by flowing backwash liquid upwardly through the bed to expand the media layers substantially in situ to remove the contaminants. Next, the bed is reformed with substantially distinct layers. Due to the uniformity in both size and shape of the granules in the top layer, a porosity at the entrance surface in the top layer is achieved which is substantially the same as the porosity of the upper layer surface prior to the filtration cycle. Accordingly, the rate of pressure buildup during subsequent filtration cycles should be about the same as in the initial filtration cycle. This is contrary to prior art methods where the filter material is not highly uniform in size, resulting in a stratification of granules after backwashing from the finest to the coarsest and causing increased rates of pressure buildup in subsequent filtration cycles.

Thus, one of the important objects of the present invention is to provide a method of filtering a heavy dirt load and lint like plugging materials through a filter bed consisting of a top coarse layer of bead like materials followed by one or two other granular filter medias and then backwashing the entire filter bed in situ by the upward flow of water.

It is a further object of this invention to provide a filter media that is essentially a large bead like object with a specific gravity in the range of from about 1.05 to about 1.4 and with a size larger than the anthracite normally used with the deep bed media. It is another object of the invention that the bead like material be either cylindrical or spherical in shape for presenting the greatest porosity to the filter bed. It is also a further object of the invention that the bead like materials all be uniform in size and that they are easily wetted with water or have only a mild hydrophobic tendency.

DETAILED DESCRIPTION OF THE PREFERRED EMBODIMENTS

Various materials have been investigated for their suitability as a media in a deep bed filter, either alone or in combination with other media. Based upon these investigations and their results, the present invention proposes various filter media that may be utilized either as the top layer of a multi-layer, deep bed filter or as the media in a mono-media deep bed filter. For example, the novel filter media may be used as the top filter media layer on top of a layer of either anthracite or sand in a dual-media filter. For the general operating methods and procedures of these type filters, reference is made to Applicant's U.S. Pat. Nos. 3,900,395 and 3,925,202, incorporated by reference. Alternatively, the novel filter media of this invention may be used as the top layer in a three-media deep bed filter, comprised, for example, of a bottom layer of sand and a middle layer of anthracite.

The specific materials proposed by this invention are hollow glass beads, or pellets of either nitrile rubber, polysulfide rubber or polyurethane. These particular materials have been found to possess at least some or all of the following characteristics, making them ideal for the purposes disclosed herein.

The first of these characteristics is a specific gravity within the range of from about 1.05 to about 1.4. For example, the nitrile rubber, polysulfide rubber and polyurethane all have a specific gravity of about 1.2 to about 1.3. Therefore, these materials can be extruded and chopped, in conventional-type operations, to form pellets or granules in the desired size range. Glass, however, normally has a specific gravity of about 2.5. Therefore, the present invention proposes to form hollow glass beads having an effective specific gravity of about 1.2 to 1.3. For example, standard glass-forming operations can be utilized to form a glass tube which is then pinched shut at regular intervals to form hollow granules of the desired size, shape, and specific gravity.

This particular range of specific gravity is desirable for several reasons. First, one object of this invention is to provide a multiplelayer deep bed filter which can be backwashed and rejuvenated in place, in contrast to the backwashing techniques of Applicant's prior U.S. Pat. No. 3,814,247. Therefore, the lower limit on the specific gravity must be such that the filter media of this invention will not be flushed out of the filter bed during reverse backwash flow. At the other end of the specific gravity range, the media must be heavy enough to intermix at the interface with the next adjacent, lower filter media layer, without sinking into that layer upon backwashing and losing the substantially distinct nature of the two superimposed, contiguous media layers.

The second desirable characteristic for the filter materials of this invention relates to being preferentially water-wetted, or hydrophilic, as opposed to being preferentially oil-wetted, or oleophilic. Each of the specific filter materials listed above exhibit this desirable characteristic, although to varying degrees. Specifically, glass beads exhibit the greatest degree of water-wetting and least degree of affinity for oil, and the polyurethane exhibits the mildest degree of water-wetting. It is somewhat unexpected that the rubber and polyurethane beads are suitable for the purposes of this invention because experience has shown that most polymeric, petroleum based materials have a strong affinity for oil.

By being water-wetted, or at least not highly hydrophobic, these materials are almost entirely wet by the influent liquid, minimizing the possibility that air bubbles will attach to the individual granules and alter their overall effective specific gravity. Therefore, it becomes possible to control the action of the granules during backwash. More specifically, with filter materials that are not completely water-wetted, air bubbles have a tendency to attach to the individual granules, thus altering the granule's specific gravity and enabling the granules to flow out of the filter bed during reverse backwash flow. Obviously, this result is undesirable and is effectively overcome by the specific filter materials proposed in this disclosure and their water-wetted characteristics which have been recognized by Applicant.

The third desirable characteristic for the filter material proposed by this invention relates to having the individual filter granules highly uniform in both size and shape. For example, the pellets of either nitrile rubber, polysulfide rubber, or polyurethane may be formed by extrusion and chopping to achieve highly uniform, substantially symmetrical granules. The disclosed glass granules can be manufactured in highly uniform sizes and shapes by first forming a glass tube by conventional glass forming techniques. Next, the glass tube, while at a deformable temperature, can be pinched shut at regular intervals to form capsule-shaped granules having the desired uniformity of size.

This uniformity feature yields several important results. For example, since the individual filter particles are substantially uniform in size, there is no classification or stratification of the granules, leaving this layer of filter material substantially homogeneous throughout. This also enables a high porosity at the entrance surface of the filter layer, which is very essential for dirt penetration. Further, because there is no classification or stratification of materials in the top layer of filter material, the entrance surface in the top layer has a porosity after backwashing substantially the same as the porosity of the entrance surface prior to the filtration cycle. Thus, the highly porous entrance surface is provided for subsequent filtration cycles for effective dirt penetration and a reduced rate of back pressure buildup.

This uniformity characteristic is capable of a numerical value based upon a uniformity coefficient, being defined as a numerical value obtained by dividing the sieve opening (in millimeters) which will pass sixty percent of the sample, by the sieve opening (in millimeters) which will pass just ten percent of the sample. In the present invention, it is desirable to provide a filter medium having a uniformity coefficient of substantially about one. In comparison, anthracite and sand typically have a uniformity coefficient of from about 1.3 to about 1.6, depending upon the sieving procedure, because these materials are comprised of various shaped and sized particles. However, synthetic fabricated particles of the type proposed by the present invention are not sieved because they are all made of substantially the same size.

Other desirable characteristics for the present invention include having the granules of either a spherical or cylindrical shape, the most desirable shape being cylindrical because this configuration provides a greater porosity. Further, the most desirable size for a spherical granule is an outer diameter of between about 3/16 to ¼ inch. Likewise, for cylindrical granules it is desirable to have both a length and a diameter within the range of between about 3/16 and ¼ inch. This particular size provides the porosity and filtration effect desired in relationship to an optimum back pressure buildup.

To illustrate the basic principle involved in this invention, several sets of tests have been conducted to provide direct comparison with other filter arrangements. The results from these tests clearly show the advantages and improved results of this invention.

A first set of tests was run on two test filters, where contaminated liquid was pumped to the two filters simultaneously from the same source for direct comparison. The contaminants in the water-based liquid consisted of 50 ppm (parts per million) Kaolin, 5 ppm alum and 10 ppm lint. The filtration flow rate was ten gallons per minute per square foot of cross-sectional filter area.

The first filter in this set of tests, Filter No. 1, was comprised of a bottom layer of 24 inches of 30–50 mesh sand (0.35 to 0.55 millimeters) and a top 12 inch layer of 16–20 mesh anthracite (0.8 to 1.2 millimeters), the layers being intermixed at their contacting interface.

The second filter, Filter No. 2, was comprised of a bottom 24 inch layer of 30–50 mesh sand, an intermediate 12 inch layer of 16–20 mesh anthracite and a top 9 inch layer of cylindrical nitrile rubber beads having both a length and a diameter of 3/16 inch. Again, the layers were intermixed at their contacting interfaces.

The following results were recorded:

| Filter No. 1—Total Gallons of Influent Contaminated Liquid | Turbidity in J.T.U. (Jackson Turbidity Units) | Pressure Drop in Lbs. |
| --- | --- | --- |
| 100 | .67 | 5 |
| 200 | .70 | 21 |

| Filter No. 2—Total Gallons of Influent Contaminated Liquid | Turbidity in J.T.U. (Jackson Turbidity Units) | Pressure Drop in Lbs. |
| --- | --- | --- |
| 100 | .50 | 2 |
| 200 | .46 | 2 |
| 300 | .49 | 2 |
| 600 | .42 | 2.5 |
| 1200 | .44 | 3 |

These results show that filter No. 2, representing one example of this invention, developed a pressure drop of only two pounds across the entire filter after 200 gallons contaminated liquid flow as compared to a twenty-one pound pressure drop in test filter No. 1 after the same amount of flow. These same results also show that test Filter No. 2 developed a pressure drop of only 3 pounds after a total of 1200 gallons of flow.

The comparative advantage of the present invention is therefore quite evident from this first set of tests.

A second set of tests was run on two different test filters, with results again clearly demonstrating the advantage of the present invention. In this second set of tests contaminated liquid was again pumped to the two filters simultaneously. The contaminants in the water-based liquid of this test included 50 ppm Kaolin, 5 ppm alum and 2 ppm lint. The flow rate was again 10 gallons per minute per square foot of filter bed cross-sectional area.

The first filter in this group, identified as Filter No. 3, was comprised of a bottom 24 inch layer of 30–50 mesh sand and a top 12 inch layer of 16–20 mesh anthracite. The second filter of this group, Filter No. 4, was comprised of a bottom 24 inch layer of 30–50 mesh sand and a six inch layer of cylindrical nitrile rubber beads having both a length and a diameter of 3/16 inch. Again, in both filter beds the two filter media layers were intermixed at the contacting interface.

The recorded results are as follows:

| Filter No. 3 Total Gallons of Influent Contaminated Liquid | Turbidity in J.T.U. | Pressure Drop in Lbs. |
|---|---|---|
| 100 | .50 | 1 |
| 200 | .34 | 1 |
| 300 | .30 | 1.5 |
| 400 | .26 | 3 |
| 500 | .73 | 22 |

| Filter No. 4 Total Gallons of Influent Contaminated Liquid | Turbidity in J.T.U. | Pressure Drop in Lbs. |
|---|---|---|
| 100 | 1.1 | 1 |
| 200 | .55 | 1 |
| 300 | .42 | 1 |
| 400 | .40 | 1 |
| 500 | .38 | 1 |
| 1000 | .31 | 1 |
| 2000 | .22 | 2 |
| 3000 | .18 | 3.5 |

These results show that Filter No. 4, representing another example of this invention, developed only a one pound pressure drop after 500 gallons of contaminated liquid flow, as compared with a 22 pound pressure drop with the test Filter No. 3 after the same quantity of liquid flow. Further, these results show that Filter No. 4 finally developed a pressure drop of only 3.5 pounds after a total of 3,000 gallons of liquid flow. Again, these results indicate the advantages of the present invention, as exemplified by the cylindrical nitrile rubber beads. Other similar tests have been conducted with glass beads and the same trend of a reduced rate of pressure build up was observed.

Additional observations may also be made from these tests. First, each pair of test filters provided very comparable good quality effluent. Second, each of the test filters were backwashed after a filtration cycle by reverse, expanding backwash liquid flow, after which the filters were reformed for subsequent filtration flow. In both test filters 2 and 4, the cylindrical beads in the upper layer were backwashed substantially in situ and then reformed to provide a highly porous entrance surface layer to receive further quantities of contaminated liquid flow.

It is to be understood that the present disclosure is merely exemplary in nature, rather than limiting, and that the invention is limited only by the appended claims. For example, the disclosure has described the bottom layer in the multiple-layer deep bed filter as being comprised of either sand or anthracite. Of course, it will be understood that other similar materials may likewise be utilized. Additionally, the invention has been described in terms of characteristics that have been found in four specific filter media materials. Again, it is to be understood that these particular filter materials are provided as examples of materials which provide the features set forth in the appended claims.

Having therefore completely and fully described my invention, I now claim:

1. In a method of filtering contaminants from a liquid, the steps of:
   flowing contaminated liquid through a deep bed filter comprised of at least two contiguous, vertically superimposed filter media layers, thereby accumulating contaminants within the interstices of the bed to achieve a clarified filtrate, the filter media of the uppermost of said layers (a) consisting essentially of hydrophilic, oleophobic granules substantially symmetrical and substantially uniform in size and shape to provide a porous entrance surface for the contaminated liquid, the granules having a uniformity coefficient of substantially about and not less than 1, wherein the uniformity coefficient is defined as the number obtained by dividing the sieve opening, in millimeters, which will pass sixty percent of the granules, by the sieve opening in millimeters which will pass just ten percent of the granules, and (b) having a specific gravity in the range of between about 1.05 and about 1.4;
   terminating the flow of contaminated liquid after the filter has become at least partially clogged by accumulated contaminants;
   rejuvenating the deep bed filter by flowing backwash liquid upwardly through the bed to expand both layers substantially in situ to remove accumulated contaminants, the specific gravity of the uppermost of the layers facilitating expansion for the removal of contaminants; and
   reforming the bed with substantially distinct layers subsequent to the backwashing step and achieving an entrance surface in the uppermost of said layers having a porosity substantially the same as the porosity of said surface prior to the filtration cycle.

* * * * *